United States Patent [19]

Dorokhova et al.

[11] Patent Number: 4,481,201

[45] Date of Patent: Nov. 6, 1984

[54] PHARMACEUTICAL COMPOSITION CONTAINING N,N³-DI-(β-BROMOPROPIONYL)-N¹,N²-DISPIROTRIPIPERAZINIUM DICHLORIDE

[75] Inventors: Margarita I. Dorokhova; Alla N. Zamskaya; Sofya M. Minakova; Tamara S. Safonova; Vladimir A. Chernov, all of Moscow, U.S.S.R.; Kira V. Levshina, deceased, late of Moscow, U.S.S.R.; Alexandr A. Mizeri, administrator, Moscow, U.S.S.R.; Olga Y. Tikhonova, deceased, late of Moscow, U.S.S.R.; Emilia F. Shardakova, administrator, Moscow, U.S.S.R.

[73] Assignee: Vsesojuzny Naucho-Issledovatelsky Khimoko-Farmasevtichesky Institut Imeni S. Ordzhonikidze, U.S.S.R.

[21] Appl. No.: 318,973

[22] Filed: Nov. 6, 1981

[51] Int. Cl.³ .................................. A61K 31/495

[52] U.S. Cl. .................................... 424/250

[58] Field of Search .......................... 424/250

[56] References Cited

PUBLICATIONS

Chemical Abstracts, 77: 88443v, (1972), and the 9th Coll., p. 10114f, ($C_{18}H_{32}d_2W_4O_2$).

*Primary Examiner*—Jerome D. Goldberg
*Attorney, Agent, or Firm*—Steinberg & Raskin

[57] ABSTRACT

A pharmaceutical composition intended for the treatment of an acute leukemia which comprises, as the active principle, N,N³-di-(β-bromopropionyl)-N¹,N²-dispirotripiperazinium dichloride and a pharmaceutically acceptable vehicle therefor. The active principle is used as a lyophilized powder. As the vehicle use is made of an isotonic solution of sodium chloride or distilled water. The content of the active principle in the pharmaceutical composition for injections is 2 to 5% by weight.

7 Claims, No Drawings

PHARMACEUTICAL COMPOSITION CONTAINING N,N³-DI-(β-BROMOPROPIONYL)-N¹,N²-DISPIROTRIPIPERAZINIUM DICHLORIDE

FIELD OF APPLICATION

The present invention relates to the art of medicine, and, more particularly, it relates to a pharmaceutical composition containing N,N³-di-(β-bromopropionyl)-N¹,N²-dispirotripiperazinium dichloride.

BACKGROUND OF THE INVENTION

For the treatment of malignant neoplasms, particularly acute leukemias, at the present time use is made of a great number of compositions having various chemical compounds as the active principle. (Cf. Antineoplastic and Immuno-Suppressive Agents, Springer-Vertag, Berlin-Heidelberg, New York, 1974, vol. II/1/; Chemotherapy of Solid Tumors, World Health Organization, Geneva, 1977 /2/).

Such chemical compounds can be exemplified by the following:

alkylating compounds containing 2-chloroethylamine groups (preparations: Embiquine, Melfolan, Cyclophosphamide, Leukeran, etc.) /2/, pp. 89–90;

ethyleneimine groups (preparation: ThioTEF and its analogues) /2/, p. 89;

methanesulphonic groups (preparations: Mileran, etc.), /2/, p. 90;

nitrosoalkylurea derivatives (preparations: CCNU, BCNU, methylnitrosourea and the like) /1/, pp. 65–84; /2/, p. 97;

antimetabolites of nucleic and protein exchange /2/, pp. 90–92;

analogs of pyrimidine bases (preparations: 5-fluorouracyl, cytozine arabinozide, etc.) /1/, pp. 193–271;

analogs of purine bases (6-mercaptopurine, thioguanine and the like) /1/, pp. 384–403;

folic acid antagonists (preparations: metotrexate and its analogues) /1/, pp. 468–483;

antibiotics (preparations: adriamycin, rubomycin, bleomycin, actinomycin D and the like) /1/, pp. 593–614, 850–876, 582–592; /2/, pp. 93–95;

compounds extracted from plants (preparations: kolkhycin, vinblastin, vinkrystin and the like) /1/, pp. 670–694; /2/. pp. 92–93;

other groups of antitumor compounds (preparations: Prospidin has been used in the treatment of acute leukemia /Proceedings of VNIIChFI, "Prospidin—New Antitumor Compound", iss. III, Moscow, 1973, pp. 6–16/, procarbozine /1/, pp. 829–840; /2/, p. 98.

However, in the use thereof the therapeutic effect in the majority of cases turns to be only temporary and is achieved, as a rule, by administration of doses causing the development of side effects—suppression of hemopoesis, disturbances of the function of the alimentary tract, kidneys, etc. /2/, /3/. Furthermore, in the repeated use of antitumor medicated compounds there is observed the development of a pharmaceutical adaptation to the effect of the preparation employed.

OBJECT OF THE INVENTION

It is an object of the present invention to provide a novel pharmaceutical composition employed for the treatment of an acute leukemia which would be more efficient as compared to the prior art Prospidin.

SUMMARY OF THE INVENTION

This object is accomplished by a pharmaceutical composition employed for the treatment of an acute leukemia which, according to the present invention, comprises, as the active principle, N,N³-di-(β-bromopropionyl)-N¹,N²-dispirotripiperazinium dichloride of the general formula:

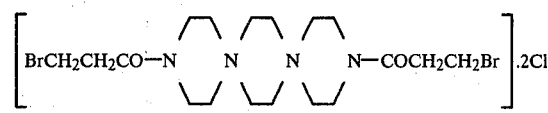

and a pharmaceutically acceptable vehicle.

BRIEF DESCRIPTION OF THE INVENTION

According to the present invention, the active principle is used as a powder (lyophilized form).

According to the present invention, the active principle in preparations for injections is used in an amount ranging from 2 to 5%.

According to the present invention, as the pharmaceutically acceptable carrier or vehicle use is made of an isotonic solution of sodium chloride, distilled water.

A detailed description of the present invention is given hereinbelow.

DETAILED DESCRIPTION OF THE INVENTION

It has been found by the inventors that quaternary salts of N,N³-di-(β-bromopropionyl)-N¹,N²-dispirotripiperazinium of the general formula (I) reveal biological activity and can be used as substances possessing an anti-leukotic effect.

In order to find out anti-acute leukemia properties and toxicity of these compounds, there have been studied:

(1) the effect of the compounds on the growth of transplantable tumors in white noninbred rats and mice;

(2) activity of the compounds relative to leukoses of inbred mice;

(3) acute toxicity of the compounds upon a single and repeated administration to white noninbred mice places into standard cages with 8 animals in each.

Biological properties of the compounds according to the present invention have been studied in experiments on rats and mice.

The antitumor activity has been studied on white rats weighing 110–130 g, as well as on white noninbred and inbred mice weighing 17–21 g with ligated tumors. The treatment is started 5–7 days transplanting of solid tumors and the following day after the transplanting of leukotic strains. Use has been made of the following transplantable strains of the tumors:

(1) rats: Ienssen's sarcoma, sarcoma 45, sarcoma M-1, sarcoma 536;

(2) noninbred white mice: sarcoma 180, sarcoma AK, sarcoma 37, carcinoma HK;

(3) inbred mice: leukemia La, leukemia L1210 and P-388.

The compounds of the general formula (I), wherein X represents Cl⁻ (compound 1), Br⁻ (compound 2) are well-soluble in an isotonic solution of sodium chloride and they are administered intraperitoneally. The doses of the compounds have been calculated in mg per kg of the animal bodyweight.

Since the compound of the general formula (I), wherein X is n-CH$_3$C$_6$H$_4$SO$_3$⁻ (compound 3) is sparingly soluble in water, it has been administered as a suspension prepared on a starch paste and the doses are also calculated in mg per kg of the animal bodyweight.

As a result of the study it has been found out that the compounds feature a pronounced antitumor activity on transplantable tumors of rats. The corresponding data are given in Table 1 hereinbelow.

As it follows from Table 1, in the use of maximum tolerable doses (MTD) of compounds 1 and 2 there is observed a considerable suppression of Ienssen sarcoma (by 98 and 100%), sarcoma M-1 (by 99 and 95%), sarcoma 45 (by 99 and 100%), sarcoma 536 (by 78 and 74%) respectively. A substantial decrease of this dose to rats with Ienssen sarcoma has not considerably affected the variation of the antitumor activity of compounds 1 and 2. Thus, upon administration of compound 1 to rats with Ienssen sarcoma in a dose 80 times smaller than its MTD (i.e. 2 mg/kg) and compound 2 in a dose 20 times smaller than its MTD (i.e. 8 mg/kg), the suppression of the tumor growth has been observed by 69 and 43% respectively.

A high antitumor activity was also observed in the case of administration of the compounds according to the present invention to white noninbred mice with transplantable tumors. The corresponding data are shown in Table 2 hereinbelow.

As it can be seen from Table 2, upon administration of compounds 1 and 2 in their MTD, there is observed the suppression of sarcoma 180 (by 66 and 52%), sarcoma 37 (by 88 and 60%), sarcoma AK (by 87 and 81%) respectively.

The activity of compounds relative to leukosis has been assessed by the life span (I$_t$) of treated animals as compared to the control ones. I$_t$—index of suppression of leukosis development is calculated by the formula:

$$\frac{\text{average life span of the treated animals}}{\text{average life span of the control animals}} \times 100 - 100$$

Compounds 1 and 2 exhibit a clearly pronounced antileukotic effect. The data are shown in Table 3.

It is seen from Table 3 that the use of MTD of compounds 1 and 2 to mice with transplantable leukemia La has extended the life span of the treated mice 3 and 2 times respectively as compared to the control. Furthermore, compound 1 has extended the life span of mice with leukemia L1210 by a factor of 1.03 and with leukemia P-388—by a factor of 2 as compared to the control.

Compound 3 has been studied on rats and mice with transplantable tumors by per os administration. In the case of MTD of compound 3 there is observed the suppression of Ienssen sarcoma growth (by 50%), sarcoma M-1 (by 49%) and sarcoma 180 (by 35)—see Tables 1 and 2.

In the investigation of toxic properties of the compounds according to the present invention there has been determined the absolutely lethal dose (DL$_{95}$), average lethal dose (DL$_{50}$) and MTD. For compounds 1 and 2 there were determined DL$_{95}$ and DL$_{50}$ on healthy white mice with the body mass of 18–21 g at a single and repeated (once a day, daily for 7 days) intraperitoneal administration.

It has been found that in a single intraperitoneal administration of compound 1 its DL$_{50}$=1,924 mg/kg; that of compound 2 under the same conditions is 1,150 mg/kg; DL$_{95}$ of compounds 1 and 2 are 2,272 and 1,250 mg/kg respectively. The data are shown in Table 4.

Upon repeated administration of compound 1 its DL$_{95}$ and DL$_{50}$ are equal to 577 and 444 mg/kg respectively; for compound 2—340 and 150 mg/kg respectively. MTD of compounds 1, 2 and 3 are 149, 125 and 83 mg/kg respectively (see Table 4).

MTD of compounds 1, 2 and 3 have been studied in therapeutical experiments on animals with graft tumors by way of repeated administration (see Tables 1 and 2).

The study of the compounds according to the present invention in comparison with the prior art preparation prospidin (otherwise, 3,12-diaza-6,9-diazaniumdispiro-[5,2,5,2]-hexadecane-3,12-bis-(3-chloro-2-hydroxypropyl)-dichloride) has been carried out in a special series of experiments.

As regards their toxicity, the compounds of the present invention are less toxic than prospidin (see Table 4).

The compounds according to the present invention are active in respect of mice with transplantable leukemia, while prospidin does not affect the development of leukemiae (see Tables 3 and 5).

As it is seen from Table 5, an essential advantage of the compounds according to the present invention over prospidin resides in a wide range of its therapeutical effect. Thus, if the chemotherapeutical index (Ch/T) of prospidin on Ienssen sarcoma is equal to 27, for compounds 1 and 2 it is equal to 60 and 50 respectively, i.e. it is twice higher than for prospidin.

The most active, among the above-specified compounds, is N,N$^3$-di-($\beta$-bromopropionyl)-N$^1$,N$^2$-dispirotripiperazinium dichloride which is useful as the active principle of a new preparation for the treatment of acute leukemia according to the present invention.

The study of pharmacological activity of the medicated compound according to the present invention on animals (rats and mice) has been carried out in comparison with prospidin.

The medicated compound according to the present invention possesses a considerable anti-acute leukemia effect not only when administered intraperitoneally, but hypodermally and intramuscularly as well. The respective data are shown in Table 6. Furthermore, the preparation according to the present invention is more effective than prospidin when administered per os to rats with Ienssen sarcoma. The results are shown in Table 7.

The preparation according to the present invention has a pronounced antileukotic effect, whereas prospidin does not provide any effect on transplantable leukemia in mice (see Table 5).

The medicated compound according to the present invention has a 2.5-fold wider range of therapeutical action as compared to prospidin (cf. Table 5).

In the comparative study of toxicity of the preparation according to the present invention and prospidin it has been found that it is 2 times less toxic than prospidin (DL$_{50}$) of the preparation according to the present invention at a single administration to mice weighing 20–21 g is 1,924 mg/kg, while that of prospidin under the same conditions is 1,000 mg/kg (see Table 4).

The compound according to the present invention has a more pronounced cumulative effect of the toxic effect than prospidin (cf. Table 4).

Furthermore, the particular distribution of the preparation according to the present invention within organs and tissues should also be noted. The data are shown in Tables 8 and 9.

In the case of administration of the preparation according to the present invention labeled with $C^{14}$, a higher level of radioactivity in blood is observed than in the case of prospidin labeled with $C^{14}$. A higher rate of accumulation of the preparation according to the present invention as compared to prospidin is observed in larynx, windpipe, bronchi, bone marrow, tumor and thyroid gland. The preparation according to the present invention labeled with $C^{14}$ is withdrawn from the organism within 24 hours after the intravenous administration mainly with urine, while $C^{14}$—labeled prospidin is retained in the organism for a longer period. The corresponding data are shown in Table 10.

In view of these data $N,N^3$-di-($\beta$-bromopropionyl)-$N^1,N^2$-dispirotripiperazinium dichloride is proposed to be used as an active principle in a novel preparation for treating acute leucosis.

The study of the pharmacological activity of the medicated preparation of the invention on animals was carried out also in comparison with Phopurine (2-dimethylamino-6-diethyleneimido-phosphamido-7-methylpurine) employed for treating acute leukemia (U.S. Pat. No. 4,122,173).

The medicated preparation of the invention, as compared to Phopurine, exhibits a higher activity on transplantable tumors of rats and mice and has a different spectrum of action.

The expression "a different spectrum of antitumor action" of the preparation of the invention is used to imply that it causes a 78% inhibition of the growth of sarcoma 536 and a 74% inhibition of the growth of sarcoma 180, whereas Phopurine does not affect the growth of sarcoma 536 slows down the growth of sarcoma 180 by as little as 36% (see Table 5).

In its antileucotic action with regard to leukemia La the preparation of the invention is comparable to Phopurine (see Tables 3, 4, 5).

However studies have revealed a considerably smaller toxicity of the preparation of the invention in comparison with that of Phopurine. Thus, $LD_{50}$ of the preparation of the invention, in case of single administration thereof to mice is 1924 mg/kg, whereas $LD_{50}$ of Phopurine under the same conditions is 280 mg/kg (see Table 4).

The medicated composition may be used for parenteral administration in the form of solution for injections and is a solution comprising an active principle in the form of a powder (lyophilized form) in a pharmaceutically acceptable vehicle.

As the pharmaceutically acceptable vehicle use can be made of a solution of sodium chloride, distilled water.

It is advisable to use the solution of the active principle in a concentration of from 2 to 5% in the pharmaceutically acceptable vehicle.

The solution for injection is prepared directly before use by dissolution of a sterile powder (lyophilized form) in an isotonic solution of sodium chloride, distilled water.

The preparation according to the present invention has been studied in two clinics on patients with different localization of the tumoral process; the tests have justified its low toxicity.

Moreover, it has been found that the preparation according to the present invention when administered intravenously in single doses of from 500 to 600 mg daily (up to 10 g for 20 days on the whole) is well tolerated by patients.

The efficiency of the preparation according to the present invention has been also revealed for the case of acute leucosis. 54 patients were under observation including 20 patients with malignant blood diseases. In all the patients both before and after the course of treatment with the medicated compound according to the present invention the clinical state has been assessed (general state, presence of increased lymphatic nodes, liver and spleen). There were also carried out the analyses of peripheral blood, bone marrow, urine, as well as biochemical blood characteristics and electrocardiographic data (ECG). It has been found that the preparation according to the present invention, when administered intravenously in the doses of from 100 to 1,000 mg causes positive effect in 45% of patients; in 20% of patients suffering from acute lympho- and mieloregional leukemiae a complete clinicohematological remission is obtained.

Given below is an example illustrating the method for preparing $N,N^3$-di($\beta$-bromopropionyl)-$N^1,N^2$-dispirotripiperazinium dichloride.

To a mixture of 3 g of $N^1,N^2$-dispirotripiperazinium dichloride, 1.5 g of lithium hydroxide, 1 ml of water and 10 ml of ether a solution of 5.2 g of $\beta$-bromopropionic acid chlorid in 5 ml of ether is added under vigorous stirring and at a temperature of 5° to 10° C. The reaction mass is stirred for 2 hours at the temperature of 15° C. The residue is filtered off, dissolved in 10 ml of water; the resulting aqueous solution is poured in 100 ml of methanol. The obtained mixture is cooled to 0° C., the resulting residue is filtered off, washed with alcohol, and dried to give 2 g of $N,N^3$-di($\beta$-bromopropionyl)-$N^1,N^2$-dispirotripiperazinium dichloride in the form of a white crystalline substance having no characteristic melting point, well soluble in water, substantially insoluble in organic solvents.

Found, %: C 37.8; H 5.78; N 9.85; $Cl^-$ 12.21 $C_{18}H_{32}Br_2Cl_2N_4O_2$. Calculated, %: C 38.10; H 5.65; N 9.89; $Cl^-$ 12.53.

The initial compounds employed in the above example are described in the literature and obtained by way of a known method. (Proceedings of VNIIChFI "Prospidin—New Antitumor Compound", Issue III, Moscow, 1973, pp. 14–15).

TABLE 1

Effect of the compounds of the invention on growth of graft tumors in rats

| Tumor | Compound 1 Dose, mg/kg (intraperitoneally) | Compound 1 Number of injections | Compound 1 $I_t$, % | Compound 1 Change in the animal body weight, g test | Compound 1 Change in the animal body weight, g control | Compound 2 Dose, mg/kg (intraperitoneally) | Compound 2 Number of injections | Compound 2 $I_t$, % | Compound 2 Change in the animal body weight, g test | Compound 2 Change in the animal body weight, g control | Compound 3 Dose, mg/kg per os | Compound 3 Number of injections | Compound 3 $I_t$, % | Compound 3 Change in the animal body weight, g test | Compound 3 Change in the animal body weight, g control |
|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 |
| Iens-sen sar-coma | 160* | 7 | +98 | −12 | +25 | 149* | 5 | +100 | −30 | +3 | 83** | 7 | 50 | −7 | +3 |
| | 125 | 7 | +89 | +4 | −16 | 86 | 4 | +99 | +1 | +3 | | | | | |
| | 90 | 7 | +86 | +6 | −16 | 88 | 5 | +99 | +1 | −2 | | | | | |
| | 40 | 5 | +85 | +20 | +17 | 39 | 5 | +99 | +14 | +3 | | | | | |
| | 20 | 7 | +98 | +30 | +25 | 21 | 44 | +90 | +34 | +3 | | | | | |
| | 10 | 7 | +93 | +4 | +25 | 8 | 7 | +43 | +21 | −12 | | | | | |
| | 6 | 6 | +80 | +10 | +5 | 4,2 | 7 | +35 | +6 | −12 | | | | | |
| | 4 | 6 | +81 | 0 | +5 | 2,1 | 7 | +46 | +5 | −12 | | | | | |
| | 2 | 6 | +69 | −1 | +5 | | | | | | | | | | |
| | 1 | 7 | 0 | −2 | | | | | | | | | | | |
| Sar-coma 45 | 125* | 5 | +99 | −3 | +3 | 95* | 6 | +100 | −6 | −19 | not studied | | | | |
| | 80 | 5 | +99 | −9 | −12 | 83 | 7 | +96 | +6 | −4 | | | | | |
| | 50 | 7 | +61 | −8 | −12 | 44 | 7 | +96 | +4 | −4 | | | | | |
| | 20 | 7 | 0 | −12 | −12 | 20 | 7 | +66 | −12 | −4 | | | | | |
| Sar-coma 536 | 140* | 6 | +78 | −32 | +13 | 133* | 5 | +74 | −14 | −4 | not studied | | | | |
| | 70 | 6 | +55 | −22 | +13 | 81 | 6 | +52 | −15 | −4 | | | | | |
| | 50 | 7 | +45 | −15 | −14 | | | | | | | | | | |
| Sar-coma M-1 | | | | | | | | | | | not studied | | | | |
| | 111* | 5 | +99 | +4 | +14 | 95* | 6 | +97 | +8 | +21 | 85** | 6 | +49 | +1 | −3 |
| | 90 | 5 | +96 | +7 | +8 | | | | | | | | | | |

*Maximum tolerable dose (MTD)
**One experiment performed
$I_t$, % - tumor growth suppression index

TABLE 2

Effect of the preparation of the invention on growth of graft tumors in mice

| | Compound 1 | | | |
|---|---|---|---|---|
| Tumor | Dose, mg/kg (intraperitoneally) | Number of injections | $I_t$, % | Change in the animal bodyweight, g test | Change in the animal bodyweight, g control |
| Sarcoma 180 | 262* | 6 | +66 | −6 | −2 |
| | 75 | 6 | +74 | −4 | −5 |
| | 25 | 6 | +42 | | |
| Sarcoma 37 | 277* | 6 | +88 | −4 | −3 |
| | 150 | 5 | +53 | | |
| | 75 | 7 | +74 | −2 | −2 |
| Sarcoma AK | 250* | 6 | +87 | −3 | −3 |
| | 200 | 5 | +64 | | |
| | 125 | 6 | +62 | −1 | −3 |
| | 75 | 8 | +81 | −3 | −3 |
| Carcionoma HK | 250* | 6 | +86 | −4 | −2 |
| | 125 | 6 | +42 | −3 | −2 |

*maximum tolerable dose (MTD)
**one experiment performed
$I_t$, % - tumor growth suppression index

TABLE 3

Life span of mice with transplantable leukemia L1210, La and P-388 after treatment with the preparation of the invention in comparison with Prospidin and Phopurine

| Preparation | L1210 days | L1210 $I_t$ % | La days | La $I_t$ % | P-388 days | P-388 $I_t$ % |
|---|---|---|---|---|---|---|
| Preparation of the invention | 10.6 ± 2 | 38 | 21.2 ± 0.1 | 218 | 19.7 ± 0.2 | 103 |
| Prospidin | 8.1 ± 0.1 | 0 | 6.6 ± 0 | 0 | 14.8 ± 0.3 | 50 |
| Control* | 7.7 ± 0 | | 6.7 ± 0 | | 9.7 ± 0 | |
| Phopurine | — | | 22.5 ± 3.4 | 204 | | |
| Control** | — | | 7.4 ± 0.8 | | | |

*Control for the preparation of the invention and Prospidin
**Control for Phopurine

TABLE 4

Comparative data on toxicity of the compound of the invention, Prospidin and Phopurine (intraperitoneal administration to mice)

| Preparation | Singly DL$_{95}$ mg/kg | Singly DL$_{50}$ mg/kg | Repeatedly DL$_{95}$ mg/kg | Repeatedly DL$_{50}$ mg/kg | MTD | $I_k$* |
|---|---|---|---|---|---|---|
| Preparation of the invention | 2272 | 1924 | 577 | 444 | 149 | 82 |
| Prospidin | 1200 | 1000 | 250 | — | — | 58 |
| Phopurine | 430 | 280 | — | — | 120 | 12 |

*$I_k$ - index of toxic effect cumulation

TABLE 5

Range of antitumor effect of the preparation of the invention in comparison with Prospidin and Phopurine

| Preparation | Rats | | | | Mice | | | | Ch/T** |
|---|---|---|---|---|---|---|---|---|---|
| | Ienssen sarcoma | Sarcoma 45 | Sarcoma M-1 | Sarcoma 536 | Sarcoma 180 | Leukemia La | Leukemia L1210 | Leukemia P-388 | |
| Preparation of the invention | ++++ | ++++ | ++++ | ++ | ++ | 218* | 38* | 103−* | 60 |
| Phopurine | ++++ | ++++ | | 0 | + | 204 | | | |
| Prospidin | ++++ | ++ | ++++ | ++ | ++ | 0* | 0* | 50* | 27 |

Note:
++++- tumor growth suppression by 95-100%;
+++- tumor growth suppression by 80-95%;
++- tumor growth suppression by 60-80%;
+- tumor growth suppression by 30-60%;
0 - no effect.
*Index of tumor growth suppression
**Ch/T − chemotherapeutical index (ratio of the maximum tolerable dose (MTD) to the minimum effective one (ED).

TABLE 6

Effect of the preparation of the invention on the growth of graft Ienssen sarcoma upon hypodermal and intramuscular administration

| Route of administration | Dose of compound 1, mg/kg | Number of injections | $I_t$, % | Change in the bodyweight of animals, g | |
|---|---|---|---|---|---|
| | | | | test | control |
| hypodermally | 68.6 | 5 | +86 | −6 | −14 |
| intramuscularly | 55.5 | 6 | +78 | −11 | −2 |

TABLE 7

Comparative data on the effect of the composition of the invention and Prospidin on the growth of Ienssen sarcoma in rats when administered per os

| Preparation | Dose of the preparation, mg/kg | Number of injections | $I_t$, % | Change in the bodyweight of animals, g | |
|---|---|---|---|---|---|
| | | | | test | control |
| Compound 1 | 142 | 7 | +55 | −15 | −4 |
| Prospidin | 145 | 7 | +30 | −9 | −4 |

TABLE 8

Distribution of the composition of the invention within rats' organs and tissues with sarcoma M-1 after intravenous administration

| Organ | 15 min | 30 min | 60 min | 24 hours |
|---|---|---|---|---|
| Larynx | 4.15** | 3.43** | 2.0** | 0.58** |
| Kidneys | 10.4 | 5.4 | 2.6 | 0.53 |
| Bronchi | 3.4 | 2.83 | 1.7 | 0.24 |
| Windpipe | 7.29 | 4.62 | 4.64 | 0.6 |
| Hypophysis | 6.3 | 6.67 | 5.13 | 4.12 |
| Tyroid gland | 3.5 | 2.73 | 1.43 | 0.48 |
| Bone marrow | 3.84 | 6.67 | 3.78 | 0.76 |
| Thymus gland | 1.67 | 0.71 | 0.54 | 0.2 |
| Tumor | 1.76 | 0.91 | 0.57 | 0.26 |
| Blood | 1.43 | 0.91 | 0.47 | 0.05 |
| Liver | 0.94 | 0.69 | 0.76 | 0.32 |
| Spleen | 0.66 | 0.33 | 0.32 | 0.11 |
| Lungs | 0.95 | 0.71 | 0.86 | 0.26 |
| Lymphonodes | 0.69 | 0.11 | 0.69 | 0.2 |

*Compound 1 is labeled at the dispirotripiperazinium moiety of the molecule
**Coefficients of differential accumulation

TABLE 9

Distribution of Prospidin-$C^{14}$* within organs and tissues of rats with sarcoma M-1 after intravenous administration

| Organ | 15 min | 30 min | 60 min | 24 hours |
|---|---|---|---|---|
| Larynx | 0.42** | 0.32** | 0.14** | 0.05** |
| Kidneys | 3.34 | 0.67 | 0.56 | 0.15 |
| Bronchi | 2.16 | 0.82 | 0.5 | 0.25 |
| Windpipe | 0.38 | 0.21 | 0.1 | 0.07 |
| Hypophysis | 2.4 | 1.65 | 1.47 | 0.55 |
| Tyroid gland | 1.2 | 1.06 | 0.75 | 0.22 |
| Bone marrow | 0.8 | 0.6 | 0.52 | 0.18 |
| Thymus gland | 0.16 | 0.06 | 0.05 | 0.02 |
| Tumor | 0.65 | 0.37 | 0.3 | 0.07 |
| Blood | 0.4 | 0.1 | 0.07 | 0.01 |
| Liver | 1.43 | 0.75 | 0.67 | 0.13 |
| Spleen | 0.43 | 0.21 | 0.11 | 0.06 |
| Lungs | 1.54 | 0.45 | 0.2 | 0.06 |
| Lymphonodes | 0.57 | 0.48 | 0.14 | 0.04 |

*Prospidin is labeled at the dispirotripiperazinium moiety of the molecule
**Coefficients of differential accumulation

TABLE 10

Withdrawal of radioactivity from the rats' organism 24 hours after the intravenous administration of compound 1-$C^{14}$ and Prospidin-$C^{14}$

| Preparation | Urina | Feces | Total |
|---|---|---|---|
| Compound 1 | 98.3%* | 1.6% | 99.9% |
| Prospidin | 68.0 | 7.0 | 75.0 |

*80.7% are withdrawn within 3 hours.

What is claimed is:

1. Composition for the treatment of acute leukemia, comprising as active principle an acute leukemia treatment effective amount of N,$N^3$-di-($\beta$-bromopropionyl)-$N^1$,$N^2$-dispirotripiperazinium dichloride and a pharmaceutically acceptable vehicle.

2. Composition as claimed in claim 1, wherein said active principle is used as a lyophilized powder.

3. Composition as claimed in claim 1, wherein the pharmaceutically acceptable vehicle is a vehicle for injection and wherein the content of the active principle for injections is 2 to 5% by weight.

4. Composition as claimed in claim 3, wherein the pharmaceutically acceptable vehicle is an isotonic solution of sodium chloride.

5. Composition as claimed in claim 3, wherein the pharmaceutically acceptable vehicle is distilled water.

6. Method of treating acute leukemia, which comprises administering to a patient suffering from the same an acute leukemia treatment effective amount of N,$N^3$-di-($\beta$-bromopropionyl)-$N^1$,$N^2$-dispirotripiperazinium dichloride.

7. Method according to claim 6 wherein the administration is by injection.

* * * * *